United States Patent [19]

Axelgaard et al.

[11] 4,326,534

[45] Apr. 27, 1982

[54] TRANSCUTANEOUS ELECTRICAL MUSCLE STIMULATION FOR TREATMENT OF SCOLIOSIS AND OTHER SPINAL DEFORMITIES

[76] Inventors: Jens Axelgaard, 10440 Paramount Blvd., J-180, Downey, Calif. 90241; David C. Howson, 4505 Oakland Ave. South, Minneapolis, Minn. 55407; John A. Perhay, W. Hidden Valley Rd., Savage, Minn. 55378

[21] Appl. No.: 50,760

[22] Filed: Jun. 21, 1979

[51] Int. Cl.³ ............................................. A61N 1/36
[52] U.S. Cl. ............................................. 128/421
[58] Field of Search .................. 128/419 R, 421, 422, 128/423 R

[56] References Cited

U.S. PATENT DOCUMENTS

| | | | |
|---|---|---|---|
| 3,718,132 | 2/1973 | Holt et al. | 128/421 |
| 3,724,467 | 4/1973 | Avery et al. | 128/419 R |
| 3,833,005 | 9/1974 | Wingrove | 128/419 P |
| 3,911,930 | 10/1975 | Hagfors et al. | 128/421 |
| 3,983,881 | 10/1976 | Wickham | 128/421 |
| 4,026,301 | 5/1977 | Friedman et al. | 128/419 R |

OTHER PUBLICATIONS

Annual Reports of Progress, Rehabilitation Engineering Center at Rancho Los Amigos Hospital, Dec. 1976–Jan. 1978, pp. 1–2.

*Primary Examiner*—William E. Kamm
*Attorney, Agent, or Firm*—Orrin M. Haugen; Thomas J. Nikolai

[57] ABSTRACT

A method and apparatus for treatment of spinal deformities, for example, scoliosis, in which a muscle stimulator (pulse generator) is used to apply a preferred form of stimulating impulses to a patient so as to involuntarily cause contraction of particular selected trunk muscle groups to thereby effect a curvature correcting movement of selected spinal vertebrae while minimizing undesirable side effects, such as muscle fatigue. A first integrated circuit timer establishes a selectively variable "on-time" for a burst of pulses while a second such timer sets the "off-time" or interval between bursts. The individual pulses in the burst are initially of narrow width, but succeeding pulses in the group are of increasing width up to a predetermined maximum which maximum level is maintained for a desired time ("hold-time") prior to the termination of the burst. In an alternative embodiment, the stimulating impulses may be gradually decreased in width immediately prior to the pulse generator's effective "off-time". It has been determined that this pattern of stimulating pulses, when applied via body contacting electrodes positioned proximate the trunk muscle groups judiciously selected and determined by observations of the spinal curve to be corrected, has particular efficacy in the treatment of scoliosis, kyphosis, lordosis and combinations thereof.

15 Claims, 7 Drawing Figures

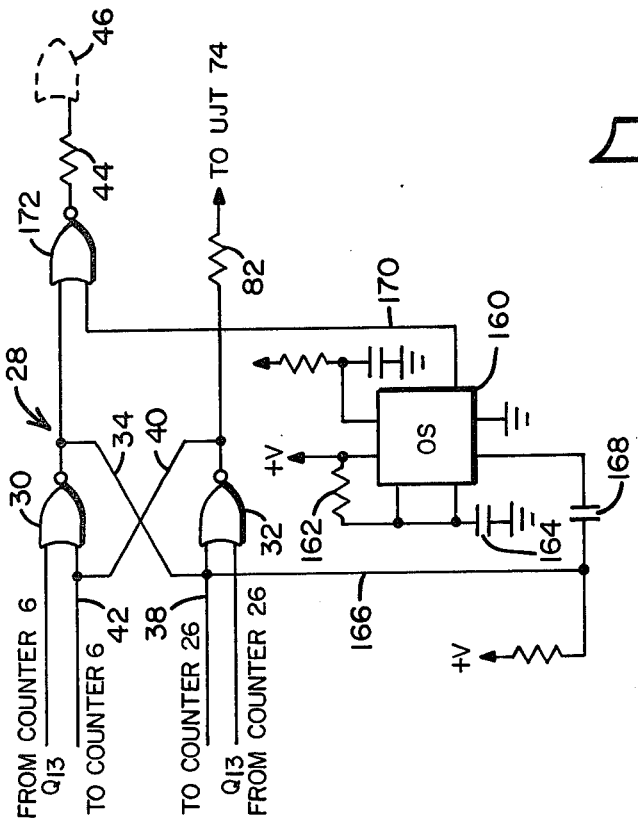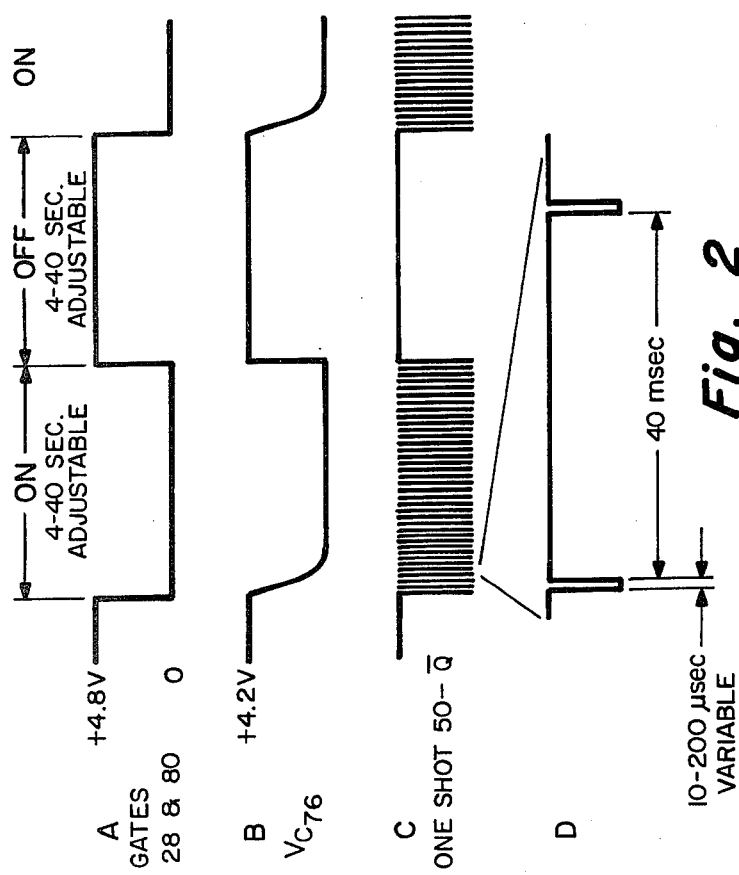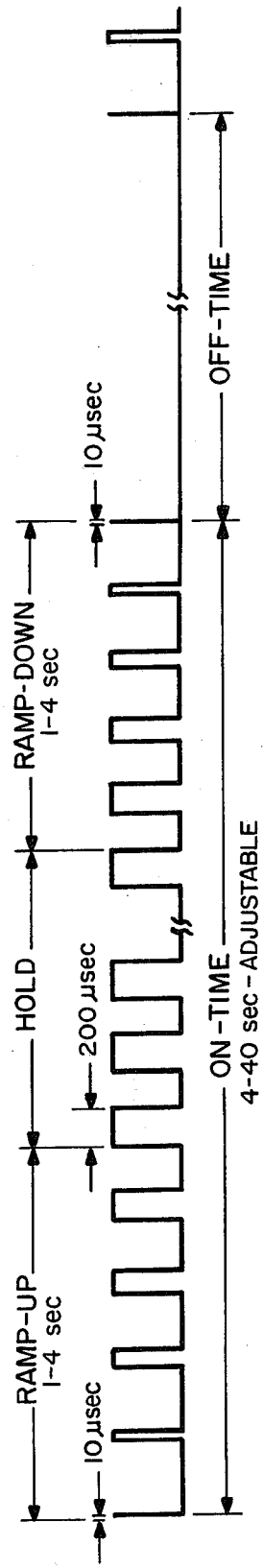

① MEDIAL (PARASPINAL MUSCLE AREA)

② INTERMEDIATE

③ LATERAL (AREA OF THE POSTERIOR AXILLARY LINE)

TRANSCUTANEOUS ELECTRICAL MUSCLE STIMULATION FOR TREATMENT OF SCOLIOSIS AND OTHER SPINAL DEFORMITIES

BACKGROUND OF THE INVENTION

I. Field of the Invention

This invention relates generally to electrical stimulating apparatus and its manner of use in the treatment of physical ailments, and more specifically to a portable, self-contained pulse generator apparatus for producing bursts of stimulating pulses at desired rates and of progressively changing pulse widths, which when applied to a patient via body contacting surface electrodes, results in rhythmic contractions of selected muscle groups and either a rapid or a gentle relaxation of these muscle groups, thereby non-voluntarily exercising and strengthening them while simultaneously evoking a corrective movement of spinal vertebrae at a predetermined site or sites along the spinal column.

II. Discussion of the Prior Art

Heretofore, the most commonly employed treatment for mild-to-moderate scoliosis and other spinal deformities in children and adolescents has involved the use of body enclosing braces for maintaining the spinal column in a desired orientation by an orthosis as the skeletal system develops. This mode of treatment suffers a number of drawbacks. First of all, such a brace is non-cosmetic in appearance, restrictive in physical activities, and not particularly acceptable to psychologically sensitive adolescent patients because it tends to set them out as being different as far as their peers are concerned. Further, the treatment involving the use of a brace generally requires the patient to be confined therein for a twenty-three hour period each day and, unless it is carefully and properly fitted, it may lead to pressure sores and other irritations. Many patients are reluctant to wear the brace faithfully and, as a result, the spinal curvature may increase to a point where surgical correction (instrumentation and/or fusion) is necessitated.

A more recent and promising alternative to bracing involves the use of electrical muscle stimulation. In the Friedman et al U.S. Pat. No. 4,026,301 there is disclosed a system for electrical treatment of spinal curvature (scoliosis) in which an electronic stimulator is implanted in the body of a patient and a plurality of cork-screw type leads are positioned medially in the paraspinal musculature proximate the apex of the primary scoliotic curve. The pulse generator applies constant width impulses during successive "on" periods which are separated by an "off" period for the sole purpose of strengthening the muscles.

In the Wickman U.S. Pat. No. 3,983,881 there is also described an electronic stimulator circuit for applying electrical stimulating signals by way of body contacting surface electrodes to medial muscle groups on the concave side of a spinal curvature (scoliosis), the pattern of pulses being such as to periodically contract and relax these muscles in a rhythmic fashion, again to strengthen the selected muscles.

The apparatus and technique described in the Friedman et al Patent suffers from several serious drawbacks. First of all, with the implanted method, the lead wires used to couple the output from the pulse generator to the cork screw electrodes have not been able to withstand the millions of flexions to which they are exposed and, accordingly, the failure rate of the equipment employed has been high. Secondly, if the electrodes are not properly placed during the initial implant surgery, such that the appropriate muscles are stimulated, or if the electrode placement causes stimulation of an intercostal nerve bundle which creates inordinate pain, it becomes necessary to explant the device or, at least, to surgically relocate the electrodes. Another drawback of the treatment involving an implanted stimulator is that it necessarily results in explantation of the device upon treatment termination, and a disfiguring scar which may be objectionable to many patients.

The method and apparatus described in the aforereferenced Wickham Patent also has a number of significant drawbacks peculiar to it. While it overcomes some of the problems attendent in a surgically implanted approach, the Wickham method contemplates surface stimulation of midline or paraspinal musculature. Because of the limited experience using this approach, the results thereof are rather nonconclusive at the present time. However, it is believed that, to date, the use of the Wickham method has been limited to the treatment of lumbar curves only and that scolotic curvature in the thoracic region cannot be corrected or arrested using this technique because of the discomfort encountered due to excessive movement of the scapula. Then too, when surface stimulation of medial muscles is employed in an attempt to correct a primary curve, it has been found that the compensatory curve is oftentimes worsened. Also, when medial stimulation is employed, as in the Wickham and Friedman Patents, an increased extension of the spine (lordosis) is often noted. This could lead to increased permanent lordosis of the spine.

Furthermore, and as will be set out in greater detail hereinbelow, the prior art apparatus does not allow the degree of control over the stimulation pulse parameters as does the device of the present invention.

SUMMARY OF THE INVENTION

The method employed in the treatment of scoliosis and other spinal deformities in accordance with the present invention and the apparatus utilized in carrying it out are deemed to be an important and significant advance in the field. No body confining braces are needed nor is implant surgery required. Instead, a special pattern of electrical stimulating impulses is repetitively applied by way of surface electrodes to appropriately selected muscle groups, primarily to biomechanically correct spinal deformities and secondarily to strengthen the muscles. Because of the biomechanical approach used, marked improvement is also often noted, not only in the primary treated curve, but in the secondary curve or curves as well and, further, in treatment of scoliosis the method can be used to treat both thoracic, thoracolumbar, and lumbar curves.

In carrying out the method of the present invention, the prospective patient suffering from a spinal deformity is first evaluated to determine whether he or she appears to be a suitable candidate for transcutaneous electrical muscle stimulation. After application of body contacting electrodes, the muscle stimulator is connected and the patient is carefully screened for stimulation tolerance and optimum electrode location for the best acute curve correction.

The pulse generator is of a type providing bursts of relatively constant (but adjustable) amplitude impulses which increase in width from a minimum value up to a predetermined adjustable maximum and, following a predetermined time interval (the "hold period"), the width again decreases to its original minimum width value.

The impulses serve to electrically stimulate specific target muscles or muscle groups according to the aforementioned pulse burst pattern so that the muscles contract smoothly at a predetermined adjustable rate ("ramp-up" interval) remain in isotonic contraction for a predetermined adjustable period ("hold" interval), and relax at a predetermined adjustable rate ("ramp-down" interval). Without the "ramp-up" the muscle contraction will be jerky which is non-physiological an uncomfortable to the patient. The "ramp-down" is less critical to the patient's comfort and can therefore be set at zero seconds if desirable for other treatment reasons. However, it is felt that an actual "ramp-down" interval is beneficial because it prevents the spinal column from abruptly snapping back to its pre-contraction state and secondarily, it is preferred by most patients.

In the treatment of scoliosis, the stimulation target muscles lie in a band which stretches from the edge of the paraspinal muscles to the anterior axillary line. A study on the effect of electrode placement in forty patients showed that a lateral electrode position on the axillary line, on the average, gave a four-fold improvement in acute prone curvature correction over that obtainable with medial paraspinal muscle stimulation while a three to four fold improvement was seen in a location midway between the bulk of the paraspinal musculature and axillary line. For this reason and because of hyperextension experienced with medial stimulation as a side effect, the paraspinal muscles are not considered and useful for the treatment of scoliosis in this invention. A lateral electrode location on the mid-axillary line or on the posterior axillary line is most often used because the longest lever arm (ribs, or ribs and pelvis) are provided here, potentially leading to the best spine correction. Moreover, the patients can easily apply the electrodes themselves.

Based on the fact that the muscles emit heat when working, a seris of thermograms was taken of muscles being stimulated and it was found that the lateral electrode position on the mid-axillary line in this thoracic region primarily serve to stimulate the latissimus dorsi and the lateral abdominals, while locations in the lumbar region primarily would stimulate the external oblique and the lateral abdominals. Although not seen in the thermograms, probably because of tissue depth, it is believed that the intercostals in the thoracic region and the quadratus lumborum in the lumbar region are also stimulated and playing an important role in the correction of scoliosis. The resulting contraction of the target muscles at spinal levels associated symmetrically with the apex of the major curve causes the ribs in the thoracic region or the ribs and the pelvis in the lumbar region to move towards each other thereby applying corrective forces and moments on the individual vertebrae of the scoliosis curvature so that the curve unbends.

In the treatment of lordosis the stimulation target muscle group is the rectus abdominus. Regional stimulation of the rectus abdominus at the spinal level of the apex of the lordotic curvature causes muscle contraction to flex the spine so that the curves correct.

In the treatment of lordoscoliosis, the stimulation target muscles at spinal levels associated symmetrically with the apex of the combined lordosis and scoliosis curves lie in a band between the anterior axillary line and the anterior mid-line.

In the treatment of kyphosis, the stimulation target muscles is the paraspinal musculature between and bilaterally to the spinal processes. When the paraspinal musculature around the apex of the curvature is stimulated into contraction, the spinal processes and other posterior-lateral articulations are moved towards each other working as short levers for spinal extension and thereby kyphosis correction.

In the treatment of kyphoscoliosis the stimulation target muscles are the unilateral paraspinal muscles on the convex side of the combined scoliosis and kyphosis curve. Forces created have a corrective effect on both the kyphosis and the scoliosis.

The treatment procedure is preferably (but not necessarily) conducted while the patient is in bed and sleeping in the prone position. As such, the engagement between the patient's upper torso and his pelvic area with the mattress tends to hold the external body against movement and, hence, the spine may be moved relative to the rather stationary pelvic and chest structures, this being the biomechanic reason for the correction of compensatory curve(s).

As mentioned, the stimulation therapy is preferably applied during the hours of sleep. This results in complete treatment privacy and, perhaps more importantly, at a time in which the antagonist muscles do not come into play to offset the effectiveness of the contractions of the desired selected muscle groups. The stimulation is applied with an on-off ratio of, for example, approximately $\frac{1}{2}$ to $\frac{1}{4}$ to reduce muscle fatigue. Using monosphasic stimulus phase with no DC component of, for example, 200 microsecond duration and about 25 pulses per second, tests to date have shown that marked improvement has occurred in the patients selected for treatment. For example, a six-month follow-up of 17 patients with major curves of 20 to 39 degrees and an average pretreatment monthly progression rate of 2.3 degrees per month revealed improvement (curve reduction) in four patients and arrest of progression in the rest. Not only has the major curve been corrected or the progression of curvature arrested, but also, the minor compensatory curves have tended to show the same improvement trend.

OBJECTS

It is accordingly the principal object of the present invention to provide an improved method of treating scoliosis and other spinal deformities and novel apparatus useful in carrying out the method or procedure.

Another more particular object of the present invention is to provide an improved method of treating idiopathic, neuromuscular infections or traumatic scoliosis in which electrical surface stimulation of the lateral trunk muscles is utilized to arrest the progress of the disease and to actually reduce the degree of curvature which had occurred prior to the beginning of treatment.

Another object of the invention is to provide a method for treating scoliosis in which a predetermined pattern of electrical stimulating impulses are applied by way of surface electrodes to selected lateral muscles on the body of the patient.

Yet another object of the invention is to provide a novel stimulator apparatus which is effective to produce recurring bursts of stimulating impulses separated by an off period, the individual pulses in a burst initially increasing from a narrow width to a predetermined wider width during an initial portion of a burst interval.

A still further object of the invention is to provide a stimulator apparatus suitable for use in the treatment of spinal deformities in which the stimulating impulses are applied in bursts of an adjustable rate and duty cycle, the individual bursts being comprised of pulses of varying width which divide the burst into a "ramp-up", a "hold" and a "ramp-down" portion or interval.

These and other objects and advantages of the invention will become apparent to those skilled in the art from the following detailed description of the preferred embodiment, especially when considered in conjunction with the accompanying drawings in which like numerals in the several views refer to corresponding parts.

BRIEF DESCRIPTION OF THE DRAWINGS

FIG. 2 represents the waveform of the impulses obtained from the circuit of FIG. 1;

FIG. 3 illustrates a modification which may be made to the circuit of FIG. 1;

FIG. 4 illustrates the idealized waveform of the impulses obtained from the circuit of FIG. 1 when modified as in FIG. 3;

FIG. 5 is a waveform of the stimulating pulse;

DESCRIPTION OF THE PREFERRED EMBODIMENT

Figure 1:
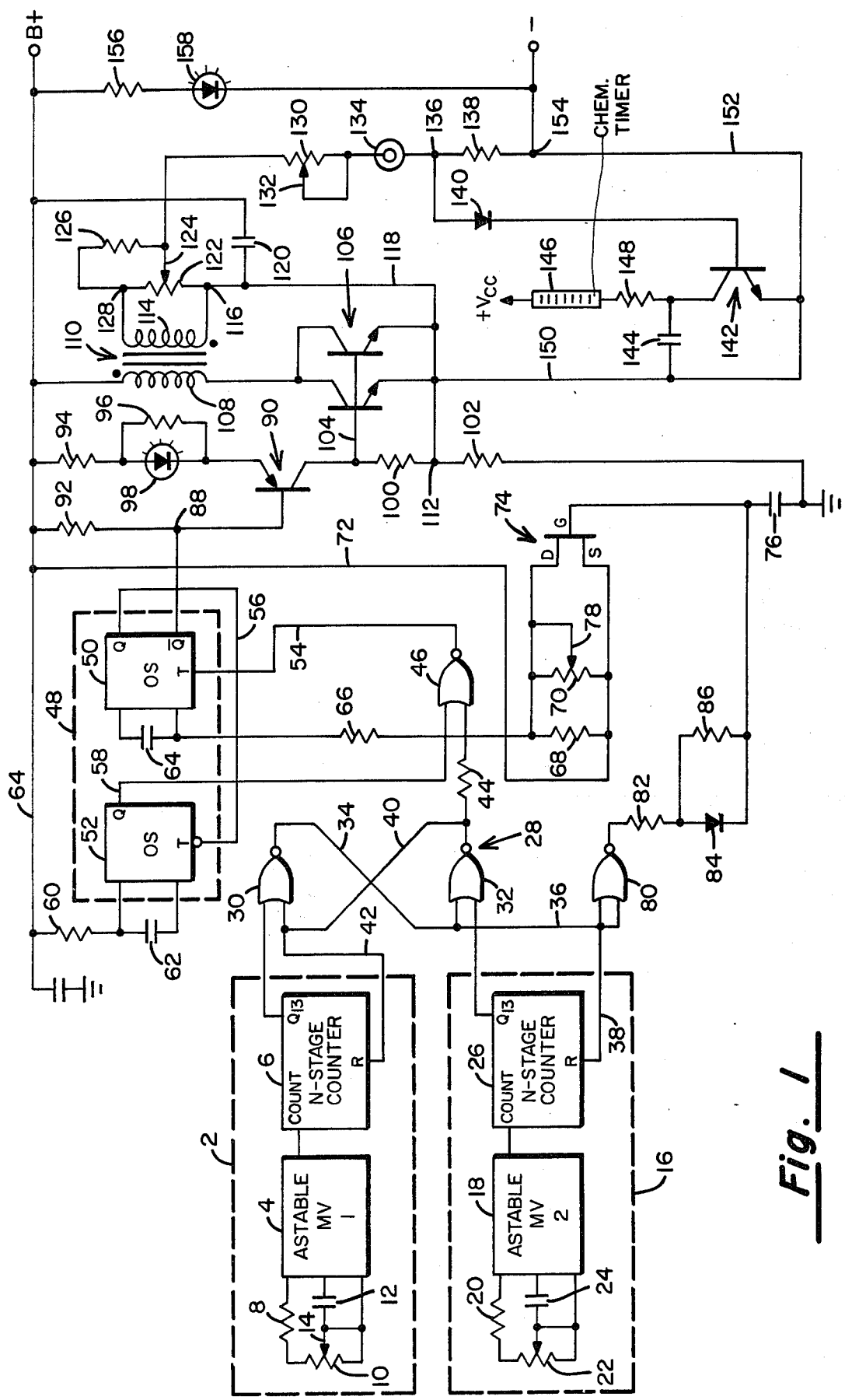
FIG. 1 illustrates by means of a schematic diagram the novel circuit configuration of a muscle stimulator useful in carrying out the treatment method of the present invention.

Referring now to FIG. 1 there is shown an electrical schematic diagram of an electronic muscle stimulator device useful in carrying out the treatment method to be described later on in this specification. Enclosed by dashed line box 2 is an integrated circuit interval timer which includes a free running oscillator in the form of the astable multivibrator 4 and a N-stage counter 6. The frequency of the output from the oscillator 4 is determined by the external R-C circuit which includes a fixed resistor 8, a variable resistor or potentiometer 10 and a capacitor 12. By positioning the wiper arm 14 of the potentiometer 10 one may charge the R-C time constant of the oscillator circuit and, hence, the frequency of its output signal. This output signal from the oscillator 4 feeds the counter 6 such that when the count developed therein reaches a predetermined value, a signal is produced indicative of this fact. Thus, one can accurately establish a given time interval by adjusting the frequency of oscillator of the oscillator feeding the counter device.

A second such integrated circuit interval timer is shown as being enclosed by dashed line box 16 and it, too, includes an oscillator in the form of astable multivibrator 18 having a frequency determining network including a fixed resistor 20, a variable resistor or potentiometer 22 and a capacitor 24 coupled to predetermined terminals thereof and a N-stage binary counter 26 having its "Count" terminal connected to the output of the oscillator 18.

A commercially available integrated circuit interval timer suitable for use as the devices 2 and 16 is the Type MC 14541 B Programmable Timer manufactured and sold by the Motorola Semiconductor Company of Phoenix, Ariz. Those skilled in the art having the specification sheets for that device, as supplied by the manufacturer, will be fully apprised as to how the circuits may be coupled to suitable power supply voltage sources and to other external circuitry for obtaining output signals a presettable time subsequent to an initial event. Hence, it is unnecessary to disclose herein the specific interconnections of the terminals of the integrated circuit chips to the external circuitry.

Associated with the output from the counter devices 6 and 26 is a flip-flop indicated generally by numeral 28 and including crosscoupled NOR gates 30 and 32. Specifically, the output from stage 13 of the counter 6 is connected as a first input to NOR gate 30 and the corresponding output from the counter 26 is connected as a first input to the NOR gate 32. The output from NOR gate 30 is connected by conductor 34 to a second input of the NOR gate 28 and to the reset terminal of the counter 26 by way of conductors 36 and 38. The output from the NOR gate 32 is connected by conductor 40 to a second input terminal of the NOR gate 30 and to the reset terminal of the counter 6 by way of conductor 42. The output from the flip-flop 28 is also coupled through a resistor 44 to a first input terminal of still a further NOR gate 46. The output from the gate 46 is coupled to a dual one-shot integrated circuit which is shown as being enclosed by dashed line box 48. For ease of explanation, the two one-shot stages comprising the integrated circuit package 48 are separately identified by numerals 50 and 52 respectively. However, in practice, the circuit 48 is a unitary chip, such as the Type 4538 B dual one-shot chips sold by the motorola Semiconductor Company of Phoenix, Ariz.

As is illustrated in FIG. 1, the output from the NOR gate 46 is connected to the trigger terminal of the one-shot circuit 50 by way of conductor 54. The Q output from the one-shot 50 is connected by a conductor 56 to the trigger input terminal of the one-shot circuit 52. The Q output from this last mentioned one-shot is coupled by conductor 58 to the second input of the NOR gate 46.

The period of instability of the one-shot circuit 52 is determined by the component values of the variable resistor 60 and the capacitor 62 which are connected in series between the one-shot 52 and the B+ bus 64. Similarly, the period of instability of the one-shot circuit 50 is governed by the component value of the capacitor 65 and the resistor network including fixed resistors 66 and 68 and the variable resistor 70. Resistors 66 and 68 are connected in series between the one-shot circuit 50 and the B+ bus 64 by a conductor 72 and the potentiometer 70 is coupled in parallel with the fixed resistor 68. Also connected in parallel with the potentiometer 70 and the source and drain electrodes of an N-channel FET device 74. The gate electrode of this device is coupled through a capacitor 76 to a point of fixed potential such as ground. The wiper arm 78 of the potentiometer 70 is also connected directly to the drain electrode of the FET device 74.

A NOR gate 80 has each of its two inputs connected to an output of the flip-flop 28 by way of conductors 34 and 36. The output of NOR gate 80 is coupled through a resistor 82 and a parallel circuit including a diode 84 and a resistor 86 to the junction point between the capacitor 76 and the gate electrode of FET device 74.

The complement output ($\overline{Q}$) of the one-shot circuit 50 is connected to a junction point 88 to which the base electrode of a semiconductor switching device 90 is connected. A resistor 92 is coupled between that junction point 88 and the B+ bus 64. The emitter electrode of the semiconductor switching device 90 is coupled through resistors 94 and 96 to the bus 64 and a LED 98 is connected in parallel with the resistor 96. The collector electrode of the NPN transistor 90 is coupled through resistors 100 and 102 to ground.

The control electrode 104 of a second semiconductor switching device 106 is connected directly to the collector electrode of the transistor 90. The primary winding 108 of an output pulse transformer 110 is connected between the B+ bus 64 and the collector electrodes of the device 106. The emitter electrodes of device 106 are connected to the junction point 112, the common point between the resistors 100 and 102. The secondary winding 114 of the transformer 110 has a first terminal 116 connected by a conductor 118 to the aforementioned junction point 112. A capacitor 120 is coupled between the terminal 116 and the bus 64. Connected directly across the secondary winding 114 of the pulse transformer 110 is a potentiometer 122 and its wiper arm 124 is connected through a resistor 126 to the other terminal of the secondary winding which is identified by numeral 128.

Connected between the junction point which is common to the wiper arm 124 and the resistor 126 is an additional potentiometer 130, the wiper arm 132 of which is connected to the remaining terminal of the potentiometer 130 and to the center terminal of a conventional coaxial jack 134. The outer terminal of the jack 134 is connected to a junction point 136 between a resistor 138 and a diode 140. The cathode of the diode 140 is connected to the base electrode of an NPN transistor 142. A capacitor 144 is connected in parallel with the collector to emitter path of the transistor 142 and a chemical timer module 146 is coupled between a source of positive potential $V_{cc}$ and the collector electrode of the transistor 142 by means of a resistor 148. The emitter electrode of the transistor 142 is connected by a conductor 150 to the emitter electrodes of the semiconductor switching device 106. The emitter of the transistor 142 is also connected by a conductor 152 to a junction point 154 to which a terminal of the resistor 138 connects. Finally, a series circuit including a resistor 156 and a light emitting diode 158 is connected between the B+ bus 64 and the junction point 154.

Now that the details of the construction of the muscle stimulating circuit of the present invention have been described, consideration will be given to the manner in which this circuit operates to produce the desired muscle stimulating waveforms.

OPERATION

The circuit shown in FIG. 1 is designed to generate a programmed series of pulses which are effective to stimulate the contraction of muscles while minimizing undesirable side effects such as muscle fatigue. Pulses are arranged in recurring bursts where the burst interval (on-time) and the interval between bursts (off-time) are independently adjustable over a desired and predetermined range. The pulse width of the individual pulses at the beginning of each burst is a preset minimum. This pulse width smoothly increases to an adjustable maximum during the initial interval of the burst and is held constant for the remainder of the burst. These features, coupled with the adjustability of the output amplitude, have been found to permit an optimum sequence to be selected for a broad range of treatment conditions.

At the outset, it should be mentioned that the resistors 8 and 10 and the capacitor 12 are chosen such that the astable multivibrator 4 will produce output pulses of a predetermined frequency. For example, component values may be selected so that as the wiper arm 14 of the potentiometer 10 is varied over its range, the multivibrator 4 may produce an output signal which varies in frequency from 102.4 Hz. to 1024 Hz.

When the flip-flop 28 formed by the cross-coupled NOR gates 30 and 32 is latched such that gate 32 is producing a low output, the 13-stage counter 6 is enabled. Hence, the astable multivibrator 4 clocks the counter, causing it to set stage $Q_{13}$ on the $4096^{th}$ count. When stage $Q_{13}$ produces its output at this count, the flip-flop 28 latches in its alternate state, thus resetting the counter 6 by way of the pulse applied to it via conductors 40 and 42. The interval thus defined corresponds to the on-time of the circuit, i.e., the time which it is operative to emit stimulating pulses. Depending upon the values chosen for the resistors 8 and 10 and the capacitor 12, this on-time interval can be varied over a nominal range of from about 3 to 30 seconds by varying the position of the wiper arm 14.

In a similar fashion, the component values of the capacitor 24 and the resistors 20 and 22 associated with astable multivibrator 18 may be chosen such that the oscillator 18 will produce an output signal of variable frequency in the range of from, say, 102.4 Hz. to 2809 Hz. as the wiper arm of the potentiometer 22 is varied over its range. The counter 26 counts these pulses to establish the off-time of the stimulator device, the off-time also being variable over a nominal range of from about 3 to 30 seconds.

Each time the flip-flop 28 changes states, it alternately enables and resets the counters 6 and 26. In this manner, the circuit will continue to cycle on and off. Because the frequencies at which oscillators 4 and 18 operate are adjustable, the overall repetition rate of the stimulation bursts is also controllable which proves most useful where it is desired to endurance train selected muscles.

With the foregoing operation and the interaction of the counters 6 and 26 and the flip-flop 32 in mind, consideration will next be given to the operation of the remaining portion of the circuit. Specifically, during the on-period when the output from the NOR gates 32 and 80 are low (see waveform A of FIG. 2), the output from NOR gate 46 goes positive, triggering the one-shot 50 and thereby causing its complementary output ($\overline{Q}$) to go low for a period determined by the time constant of the R-C network associated with its input terminals. Specifically, the component values of the capacitor 65, the resistor 66, the resistor 68 and the potentiometer 70 as well as the N-channel FET 74 determine the period of instability of the one-shot circuit 50. When the one-shot circuit 50 resets, the negative transition of its true output, Q, causes the one-shot circuit 52 to be triggered via the connection 56. The component values of the potentiometer 60 and the capacitor 62 are chosen such that the one-shot circuit 52 will remain set for a nominal period of, say, 40 milliseconds. When the one-shot circuit 52 resets, the positive transition of its Q output is inverted by NOR gate 46, causing the one-shot circuit 50 to again be triggered by the pulse applied to it via conductor 54.

In this manner, the one-shot 50 continues to generate a pulse at a constant rate of one pulse each 40 milliseconds (25 pps) during the above-mentioned on-period as is indicated by waveforms C and D in FIG. 2.

During the off-period determined by the counter 26, NOR gate 80 is producing a high output such that capacitor 76 becomes charged through resistor 82 and the parallel combination of the resistor 86 and the diode 84 to a predetermined voltage. As such, the N-channel FET device 74 becomes saturated, thereby shunting resistor 68 and potentiometer 70, leaving only resistor 66 in conjunction with capacitor 65 to determine the pulse width of the output from the one-shot circuit 50. As is indicated by the waveform B of FIG. 2, at the onset of the so-called "on-period" determined by the counter 6, the output from NOR gate 80 goes low and the capacitor 76 begins discharging through resistors 86 and 82. Initially, device 74 remains saturated which establishes a predetermined narrow width, e.g., 10 microseconds for the early pulses generated during the on-time interval. This pulse width remains substantially constant until capacitor 76 discharges to the threshold of the linear region of the FET device 74. At this time, the source to drain impedance of device 74 becomes a function of the voltage on capacitor 76, which smoothly increases as capacitor 76 further discharges. This action continues until the device 74 reaches cut-off and the individual pulses have reached their maximum width. The wiper arm 78 of the potentiometer 70 may be varied in position to establish a maximum width of, say, 200 microseconds.

Transistor 90 is maintained in a quiescent cut-off state by the bias provided at junction 88 via the resistor 92 while resistor 100 acts in a similar fashion for the semiconductor device 106. A pulse from the oneshot circuit 50 causes the transistor 90 to conduct, thus causing the semiconductor switching device 106 to saturate. Current also flows through the light emitting diode 98 which glows and thereby provides a visual indication that the device is functioning to generate pulses. Resistor 96 provides current limiting for the LED 98 while the resistor 94 provides current limiting for the transistor switching device 90.

When the device 106 saturates, a voltage pulse is impressed across the primary winding 108 of the pulse transformer 110. The turns ratio of the transformer is preferably chosen such that a voltage of a constant maximum amplitude of approximately 115 volts is developed across the secondary winding 114. Then, with the controls 124 and 132 of potentiometers 122 and 130, respectively, adjusted to their maximum position (clockwise) this pulse divides between the patient electrodes (not shown) which are adapted to be coupled to the jack 134. Turning either of the controls 124 or 132 counterclockwise will reduce the amplitude of the pulse applied to the electrodes and therefore to the patient. Because the manner in which the potentiometer 122 is connected, it provides a coarse control over the full range of from 0 to 115 volts while the potentiometer 130 provides a vernier control over a more limited range (approximately ±10%).

The chemical timer 146 is a device which provides a visual indication which is proportional to the net charge passing through it. Capacitor 144 is charged via the device 146 from the source $V_{cc}$ and resistor 148 and is discharged by way of the semiconductor switching device 142. Each pulse in each burst causes the transistor 142 to conduct by way of the ground return voltage developed across resistor 138. Each time transistor 142 is driven into conduction, it removes a specific quantity of charge from capacitor 144 which is proportional to the width of the pulse in question. As this charge is restored, the current flowing through the chemical timer 146 allows it to indicate the accumulated number of pulses provided to the patient. If the patient should remove the electrodes or if they should become unintentionally loose or disconnected, the output circuit becomes interrupted, thereby disabling the circuitry associated with the chemical timer unit. As a result, the chemical timer 146 will only provide a visual indication of the accumulated time that stimulating pulses are actually applied to the body of the patient, thus permitting trained medical personnel to evaluate more precisely the mode and efficacy of the treatment as it progresses. Resistor 148 determines the rate at which the stimulating pulses will result in a full-scale deflection of the timer unit. While a chemical timer device of the type described is wholly suitable for its intended purpose, other devices, such as a digital timer or the like may prove equally suitable.

With no limitation intended and for exemplary purposes only, the component values set forth in the following table have been determined to be usable in implementing the muscle stimulator device described herein.

TABLE I

| Resistors | |
| --- | --- |
| 8,20 | 220 Kohm |
| 10,22 | 2 Mohm - variable |
| 44 | 1 Mohm |
| 60 | 910 Kohm (variable) |
| 66,82 | 15 Kohm (variable) |
| 68 | 300 Kohm |
| 70 | 200 Kohm - variable |
| 86 | 560 Kohm |
| 92 | 10 Kohm |
| 94 | 10 ohms |
| 96 | 33 ohms |
| 100 | 1 Kohms |
| 102 | 470 ohms |
| 122 | 10 Kohms - variable |
| 126 | 2.2 Kohms |
| 130 | 470 ohms - variable |
| 138 | 27 ohms |
| 148 | 1.2 Mohms |
| 156 | 2.2 Kohms |
| Capacitors | |
| 12,24 | .0022 uf |
| 62 | .047 uf |
| 65 | .0015 uf |
| 76 | 2.2 uf |
| 120 | 470 uf |
| 144 | 1.0 uf |
| Active Devices | |
| 2,16 | Type MC 14541 B |
| 30,32,46 and 80 | Type MC 14001 B |
| 48 | Type MC 14538 B |
| 74 | PN 3686 |
| 84,140 | 1 N 4148 |
| 90 | 2 N 4126 |
| 98 | MV 3752 |
| 106 | MJE 200 |
| 142 | Type MPS 5172 |
| 158 | MV 5352 |

In the embodiment of FIG. 1, the width of the stimulating pulses at the onset of the on-period is quite narrow, e.g., 10 microseconds, but during an ensuing short interval, builds up gradually until the pulse width reaches a second predetermined value, e.g., approximately 200 microseconds. The width of the individual pulses then remains constant at this value until the end of the on-period when the pulse burst suddenly terminates. Thus, the pulse width is said to "ramp-up" and then "hold" for a prescribed period. The resulting affect on the muscle tissue to which the foregoing stimulating impulse pattern is applied is to create a contraction which increases in intensity to a maximum and which remains contracted until abruptly relaxed at the conclusion of the on-period.

It has been determined that a beneficial result is attained if the muscle group is allowed to slowly relax prior to the end of the on-time period, thus avoiding the precipitous relaxation. That is, patient comfort is increased when not only gradual contraction but also gradual relaxation of the muscle tissue results from the application of the stimulating pulse pattern thereto. Also, it is suspected that the rapid removal of the stimulating pulse may create a "snap effect" on the affected vertebrae which may prove to be counterproductive. Hence, a "ramp-down" of the width of the stimulating pulses prior to the onset of the "off-period" may be advantageous.

FIG. 3 illustrates the manner in which the circuit embodiment of FIG. 1 may be modified to incorporate this so-called "ramp-down" feature. As can be seen from FIG. 3, the circuit of FIG. 1 is modified by eliminating the NOR gate 80 and replacing it with a one-shot circuit 160 whose period of instability is controlled by the timing circuit including the potentiometer 162 and the capacitor 164. The output from gate 30 of the flip-flop 28 which appears on conductor 34 is applied via conductor 166 and capacitor 168 to the trigger input terminal of the one-shot 160. Hence, when the signal appearing on conductor 34 goes low, the one-shot circuit 160 is triggered to its metastable state where it remains for a period of time determined by the variable resistor 162 and the capacitor 164. The output from the one-shot circuit 160 is applied by way of a conductor 170 to a first input terminal of a further NOR gate 172. The gate 172 is disposed between the output from the flip-flop 28 and the input of the gate 46 of FIG. 1. Further, the output from the NOR gate 32 of the flip-flop 28 is connected to one side of the resistor 82 in FIG. 1, the other side being coupled through resistor 86 to the unijunction transistor device 74.

Now that the manner in which the circuit of FIG. 1 is modified in accordance with the diagram of FIG. 3 has been set forth, consideration will be given to the manner in which the modified circuit will produce a waveform such as indicated in FIG. 4 of the drawings, i.e., a burst of stimulating pulses in which the width of the individual pulses in the burst slowly increases during a predetermined portion of the burst from a narrow value to a relatively wide value and remain at that value for a second predetermined period and then slowly decreases back to the width of the initial narrow pulse.

As has already been explained, the circuit of FIG. 1 produces at the jack 134 a train of pulses which is turned on and off according to the settings of the potentiometers 10 and 22 respectively. At the onset of a given pulse train, the N-stage counter 6 outputs a signal which sets the flip-flop 28 to a given state in which the output from NOR gate 30 is high and the output from NOR gate 32 is low. The width of an individual pulse in the pulse train is controlled by a time constant which is the product of the value of capacitor 65 and the combination of resistors 66, 68 and 70. Hence, when the output from NOR gate 30 (FIG. 3) goes high, the output from NOR gate 32 switches to a "low" and the capacitor 76 discharges through the resistors 86 and 82. Since the voltage stored on the capacitor 76 determines the conductivity state of the UJT 74, as capacitor 76 discharges, the source to drain impedance of the UJT 74 increases from approximately 0 ohms to a very high value amounting to an open circuit condition. Thus, at the onset of the turn-on time, when capacitor 76 begins to discharge, the width of the resulting output pulse is determined by the product of capacitor 65 and resistor 66. However, after capacitor 76 has drained to substantially 0 volts, the effective short circuit across the parallel combination of resistor 68 and potentiometer 70 is removed (as UJT 74 assumes its open circuit impedance state) and the resulting pulse width of the signals in the output pulse train increase to a width determined by the product of the value of capacitor 65 and the resistor 66 in series with the parallel combination of the resistor 68 and potentiometer 70. Because the wiper arm 78 can be used to vary the effective resistance of the potentiometer, a degree of control is obtainable over the ultimate pulse width.

As was already mentioned, the output from the one-shot 50 at junction point 88 drives the transistor 90 which, in turn, drives the transistor switch 106 connected in series with the primary winding 108 of the output transformer 110. It should also be recalled at this point that the values of capacitor 62 and potentiometer 60 determine the variable repetition rate of the output pulses from the one-shot circuit 52 and since the output from this one-shot circuit is used to control the one-shot circuit 50, both the pulse width and the repetition rate of the signals appearing at the output jack 134 are determined by the control signal developed at junction point 88, i.e., the $\overline{Q}$ output of one-shot circuit 50.

When the oscillator driven counter comprising the IC circuit 2 "times out" as determined by the value settings of the capacitor 12 and the resistors 8 and 10, the output signal from NOR gate 30 of the flip-flop 28 switches to a "low" condition and this low signal is applied by way of conductor 166 and capacitor 168 to the one-shot circuit 160 of FIG. 3. It therefore causes the one-shot circuit 160 to output a "high" signal for a time interval determined by the product of the variable resistor 162 in ohms and the capacitor 164 in farads. In that this high signal is applied via the NOR gate 172, the resistor 44, and the NOR gate 46 to the one-shot circuit 50, it permits output pulses to be generated for an additional predetermined period beyond the normal termination of the output from timer 6. In that the output from the NOR gate 32 is "high" at this time, the capacitor 76 charges up through resistors 82 and 86 and, as the voltage builds up on the capacitor, the source to drain impedance of the UJT 74 decreases from a very high value to near 0, again altering the time constant of the circuit controlling the pulse width of these signals emanating from the one-shot 50.

Ultimately, the one-shot circuit 160 times out causing the signal on line 170 to assume a "low" state. Because the "off-time" determined by the IC circuit 16 is longer than the period of instability of the one-shot circuit 160, the output appearing at the jack 134 will remain at zero until such time that the oscillator driven counter 16 again outputs a high signal to the NOR gate 32, setting the flip-flop 28 and initiating a new cycle.

FIG. 4 then represents in idealized form the nature of the pulse train obtained at the output jack 134. During the "ramp-up" interval which may, for example, comprise the first one to four seconds of the "on-time", the individual pulses in the train increase in width from, for example, 10 microseconds up to 200 microseconds and then remain of constant width during the "hold" interval. Following the latter interval, which may typically last from one to twenty-eight seconds, is the "ramp-down" period which, again, is adjustable. During this period, the width of the pulses generated decreases from, for example, a 200 microsecond duration back to a 10 microsecond duration. The output then remains "off" for an adjustable interval controlled by the IC circuit 16 until the cycle is again re-initiated. The final output waveform is, therefore, a compensated monophasic pulse with a zero net DC current. In actual practice, the individual pulses in a burst may not be perfectly rectangular but may exhibit an RC decay and an overshoot as illustrated in FIG. 5. This decay is dependent upon the impedance of the load and upon the characteristics of the stimulator employed. It has been found that a certain amount of decay is acceptable, but that when the decay becomes excessive, there is an increase in pain experienced by some patients.

THE TREATMENT METHOD

Figure 6:
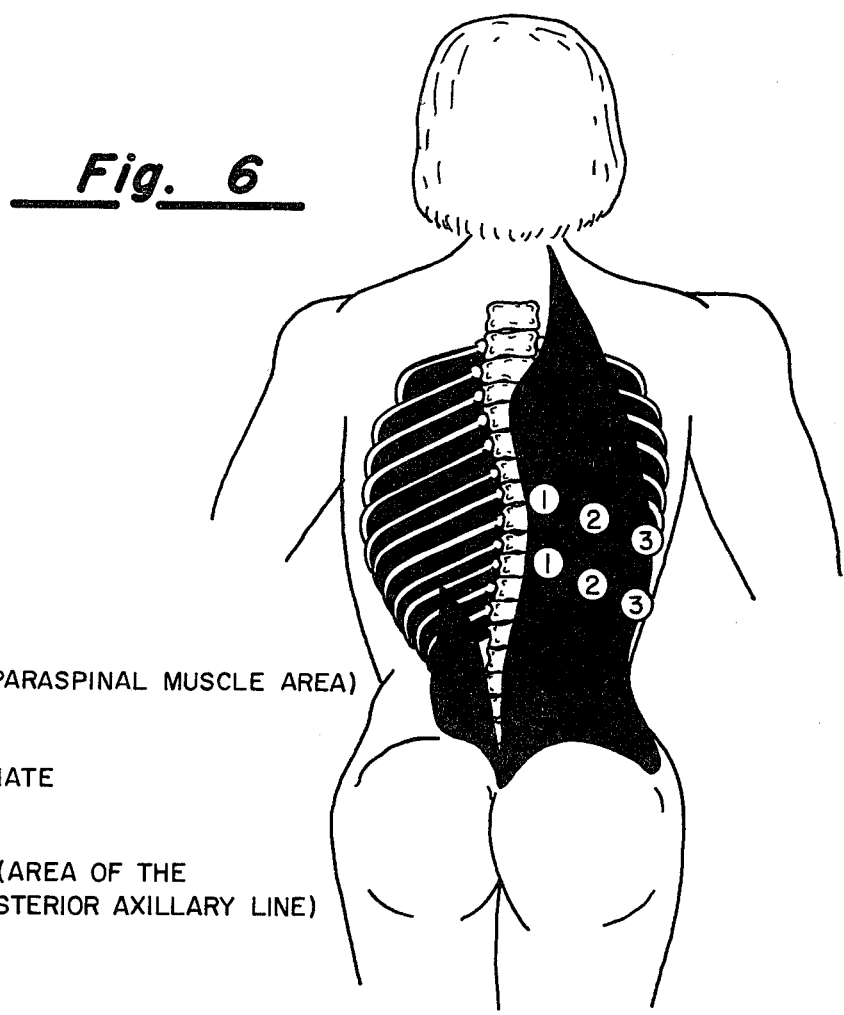
FIG. 6 is a view of a human back illustrating reference positions and electrode placement sites.
Figure 7:
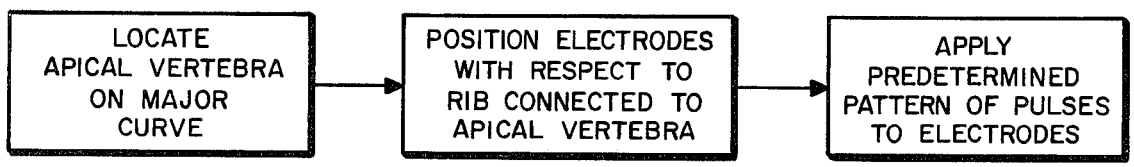
FIG. 7 is a block diagram outlining the treatment method for a scoliotic correction in the thoracic or thoracolumbar region.

With reference to FIGS. 6 and 7, in carrying out the treatment process in accordance with the present invention, patients who have been diagnosed as suffering from scoliosis, lordosis, lordoscoliosis, kyphosis, or kyphoscoliosis, are initially screened to determine whether the transcutaneous electrical muscle stimulation method of treating the disease can be utilized. In carrying out the screening process, an AP (or PA) standing X-ray of the patient is taken for scoliosis, lateral standing X-ray for lordosis and kyphosis, or an AP (or PA) and lateral standing X-rays for lordoscoliosis and kyphoscoliosis, and measurements are made thereon to determine the location of the primary and compensatory curve(s) and to determine the degree of curvature of each (degrees determined by Cobb measurement method). When the major curve to be treated is located in the throacic area, the rib joining this apical vertebra becomes the center reference in the treatment of scoliosis, lordscoliosis and lordosis. The location of the apical rib is palpatated from the apical vertebra so that site of stimulation is marked on the skin. Using the X-ray, the apical vertebra of the primary curve is located relative to, for example, the $C_7$ vertebra in the neck region, the latter being a vertebra which is easily located on the patient's back by touch. By counting down, then, it is possible to locate the apical vertebra on the body of the patient and when this has been done, the physician, again by touch and sight, follows the particular rib joined to this apical vertebra out laterally from the convex side of the scoliotic curve.

The stimulating electrodes are then placed in a symmetrical fashion above and below this center reference with the negative electrode preferably being the uppermost. Initially, the distance between the electrodes may be determined by the following guideline found from a study of 40 patients:

(a) a distance of 1 centimeter or less between electrode edges normally causes insufficient muscle contraction, (b) short curves of only few segments (3 to 5) or patients with short trunks normally require a distance between electrode edges of 2 to 4 centimeters, (c) based upon the most prevalent curve encountered, a distance of 5 centimeters between electrodes edges will normally suffice, (d) long single curves or patients with extremely long trunks will require a distance between electrode edges of from 6 to 11 centimeters.

Preferably, round electrodes 5 centimeters in diameter are used, but any electrode type of reasonable size and shape is acceptable. When round electrodes of 5 centimeters in diameter are utilized, the aforementioned distances between edges translate into the following distances between electrode centers:

(a) 6 centimeters,
(b) 7 to 9 centimeters,
(c) 10 centimeters,
(d) 11 to 16 centimeters.

With the reference center and the electrode distance selected for the curve(s) to be treated, the electrodes are located symmetrically around the reference center according to the following guideline:

(a) In scoliosis, the stimulation target muscles lie in the band which stretches from the edge of the paraspinal muscles to the anterior axillary line. Routinely, muscles in the area of the posterior axillary line or the mid axillary line are selected, thus note the 33 electrode position on FIG. 6, for example.

(b) In lordosis, the anterior midline with the rectus abdominus muscle as the target is normally selected.

(c) In lordoscoliosis, the stimulation target muscles lie between the anterior axillary line and the anterior midline.

(d) In kyphosis, the posterior midline with the paraspinal musculature on both sides of the spinal column as target is normally selected, (e) In kyphoscoliosis the target muscles are the paraspinal musculature around the apex of the curvature.

The locations where the electrodes are to be positioned are then marked with a semipermanent ink to facilitate later electrode placement by the patient or a member of the patient's family. To keep the marks visible they would have to be touched up at regular intervals. The electrodes themselves are preferably round discs formed from a conductive rubber material, the discs being approximately five centimeters in diameter and having a snap-type connector to facilitate joining the electrode to a conductive lead. The connector must be a radiopaque material like metal to show up in the X-rays. The lead, in turn, is coupled to the output jacks or terminals of the stimulator. The electrodes are electrically coupled to the skin either via electrically conductive gel or electrically conductive, flexible and adhesive disc shaped material. The electrodes and skin interface media may also be integrated into one self-contained unit.

During the initial screening process, the amplitude is adjusted to produce suitable muscle contractions, but without causing the patient undue distress or discomfort. The patient is then advised to use the stimulator during an initial two-week familiarization and muscle conditioning phase, where the amplitude of stimulation is increased every day according to the patient's increasing level or comfort. During the first week, the patient uses the stimulator during daytime only according to the following schedule in order to prevent muscle fatigue:

Day 1—½ hour three separate times;
Day 2—1 hour two separate times;
Day 3—3 hours continuously;

Day 4—4 hours;
Day 5—5 hours
Day 6—6 hours
Day 7—7 hours.

On the eighth day, the beginning of the second week, stimulation application is switched to night time while the patient sleeps. If less than 8 hours of stimulation, supplementary daytime use is required. With the presently preferred "on-off" ratio of ¼, eight hours of stimulation corresponds to three hours that the corrective force is actually applied to the spine, the remaining time being the "off" or rest portion of the cycle. After two weeks of use, the patient will return to the physician's office where an examination will be made as to whether there is any noticable skin irritation or other effects that may dictate changes of the treatment process. Possible skin irritation may be solved by the use of alternate skin interfacing materials.

Assuming that the patient does not exhibit any conditions which would preclude continued use of the method and apparatus, at the conclusion of this initial screening period, the physician more precisely locates the electrodes based on a prone X-ray of the entire spine with electrodes attached, but with no stimulation applied. In that the patient is now accustomed to the sensation of the electrical stimulation induced muscle contractions, an additional prone X-ray of the entire spine with 70 milliamps of pulse current amplitude is taken. The X-ray is measured and compared to the non-stimulated prone reference X-ray (the patient must not move between X-rays). Improvement of the major curve and no worsening of the compensatory curve(s) must be seen. If not, further electrode adjustment is necessary.

The main objective of the treatment is not principally to strengthen the muscles being stimulated, but to cause asymmetrical pressures to be exerted on growth zones so as to effect a biomechanical straightening of the spine. Specifically, by applying electrical stimulation to the surface of the skin proximate specific trunk muscles rather significant mechanical forces can be applied to the spine.

In utilizing the treatment method of the present invention, it is found that the amplitude of the stimulating pulses should be approximately 60–80 milliamperes, this value having been found to be a compromise between good muscle contractions and the lower pain threshold. However, as described above in connection with the preferred stimulator design, the amplitude is adjustable so that greater or lesser stimulating currents may be utilized. The daily treatment time may be in the range of from about four hours to about sixteen hours per day.

At periodic intervals, e.g., three months, the patient is expected to return to the physician's office so that progress may be monitored. At the time of these visits, further X-rays may be taken to ensure that electrode placement is proper, that treatment of the major curve does not adversely affect the curvature of the compensatory curve and that the curve angle has not increased further.

Upon skeletal maturity treatment is normally terminated. If the major curve has progressed more than, say five degrees, the treatment will normally be discontinued and alternate treatment intitiated, but this decision is at the physician's discretion.

The invention has been described herein in considerable detail, in order to comply with the Patent Statutes and to provide those skilled in the art with information needed to apply the novel principles, and to construct and use the specialized components as are required. However, it is to be understood that the invention can be carried out by specifically different equipment and devices, and that various modifications, both as to equipment details and operating procedures can be effected without departing from the spirit and scope of the invention itself.

What is claimed is:

1. A method of treating spinal curvature in the thoracic or thoracolumbar region of human patients comprising the steps of:
   (a) locating the apical vertebra on the major curve of the patient's spine;
   (b) positioning a pair of electrodes (1) on the outer skin surface of said patient, (2) lying within a band of muscles at a lateral trunk location and (3) generally symmetrically above and below the rib connected to said apical vertebra on the convex side of said major curve; and
   (c) repetitively applying a predetermined pattern of electrical pulses to said electrodes for evoking contraction and relaxation of preselected muscle groups in a zone defined by the location of said pair of electrodes.

2. The method as in claim 1 wherein said predetermined pattern comprises:
   (a) consecutive bursts of impulses separated by an "off period", the pulses in a burst having a relatively constant maximum amplitude and a relatively constant rate.

3. The method as in claim 2 wherein the pulses in a burst increase in width from a predetermined minimum to a predetermined maximum during a first portion of said bursts and are maintained at said predetermined maximum for a second portion of said bursts.

4. The method as in claim 3 wherein the width of the pulses in a burst return from said predetermined maximum to said predetermined minimum, during a third portion of said burst.

5. The method as in claim 4 wherein the third portion of said burst persists for a time in the range of from about zero to four seconds.

6. The method as in claim 3 wherein said first portion of said burst persists for a time interval in the range of from about one to four seconds and said second portion of said burst persists for a time interval in the range of from about zero to twenty-nine seconds.

7. The method as in claim 1 wherein said step of repetitively applying said predetermined pattern of electrical pulses to said electrodes continues for time periods in the range of from four hours to sixteen hours per day.

8. The method as in claim 1 and further including the steps of placing said patient in a prone position in a bed prior to the application of said electrical pulses to said electrodes.

9. The method of claim 1 wherein the specific spinal curvature to be treated is a scoliotic curvature and the step of positioning said pair of electrodes comprises placing said pair of electrodes within a band of muscles further defined as lying at the edge of the paraspinal muscles and the anterior axillary line.

10. The method of claim 1 wherein the specific spinal curvature to be treated is a scoliotic curvature and the step of positioning said pair of electrodes comprises placing said pair of electrodes within a band of muscles further defined as lying in the area of the posterior axillary line and the mid-axillary line.

11. A method of treating lordotic curvature of the spine in human patients comprising the steps of:
   (a) locating the apical vertebra on the major curve of said lordotic curvature to be treated;
   (b) positioning a pair of electrodes generally symmetrically above and below said apical vertebra within the zone defined by the rectus abdominus muscle group; and
   (c) repetitively applying a predetermined pattern of electrical pulses to said electrodes for evoking contraction and relaxation of said muscle group.

12. A method of treating lordoscoliotic curvature of the spine in human patients in the lumbar area comprising the steps of:
   (a) locating the apical vertebra of the major curve of the combined lordotic and scoliotic curvature to be treated;
   (b) positioning a pair of electrodes generally symmetrically above and below said apical vertebra within the muscle group lying between the anterior axillary line and the anterior mid-line; and
   (c) repetitively applying a predetermined pattern of electrical pulses to said electrodes for evoking contraction and relaxation of said muscle group.

13. A method of treating lordoscoliotic curvature of the spine in human patients in the thoracic area comprising the steps of:
   (a) locating the apical vertebra on the major curve of said scoliotic curvature to be treated;
   (b) positioning a pair of electrodes generally symmetrically above and below the rib connected to the apical vertebra, on the convex side of said lordoscoliotic curve within the muscle group lying between the anterior axillary line and the anterior mid-line; and
   (c) repetitively applying a predetermined pattern of electrical pulses to said electrodes for evoking contraction and relaxation of said muscle group.

14. A method of treating kyphotic curvature of the spine in human patients comprising the steps of:
   (a) locating the apical vertebra on the major curve of said kyphotic curvature to be treated;
   (b) positioning a pair of electrodes generally symmetrically above and below said apical vertebra within the muscle group of the paraspinal musculature bilaterally and unilaterally to the spinal process; and
   (c) repetitively applying a predetermined pattern of electrical pulses to said electrodes for evoking contraction and relaxation of said muscle group.

15. A method of treating kyphoscoliotic curvature of the spine in human patients comprising the steps of:
   (a) locating the apical vertebra on the major curve of the combined kyphotic and scoliotic curve to be treated;
   (b) positioning a pair of electrodes generally symmetrically above and below said apical vertebra, on the convex side of said combined kyphotic and scoliotic curve, within the zone defined by the paraspinal muscle group; and
   (c) repetitively applying a predetermined pattern of electrical pulses to said electrodes for evoking contraction and relaxation of said muscle group.

* * * * *

UNITED STATES PATENT AND TRADEMARK OFFICE
CERTIFICATE OF CORRECTION

PATENT NO. : 4,326,534
DATED : April 27, 1982
INVENTOR(S) : Jens Axelgaard

It is certified that error appears in the above-identified patent and that said Letters Patent are hereby corrected as shown below:

On the title page, the joint inventorship of Jens Axelgaard, David C. Howson and John A. Perhay should be changed to the sole inventorship of Jens Axelgaard.

Column 18, Line 15, Claim 14, "and unilaterally" should be deleted.

Signed and Sealed this

Thirteenth Day of July 1982

[SEAL]

*Attest:*

*Attesting Officer*

GERALD J. MOSSINGHOFF

*Commissioner of Patents and Trademarks*